United States Patent [19]
Zborowski et al.

[11] Patent Number: 6,120,735
[45] Date of Patent: Sep. 19, 2000

[54] FRACTIONAL CELL SORTER

[75] Inventors: Maciej Zborowski, Bay Village; Jeff Chalmers, Columbus; Lee R. Moore, Cleveland Heights, all of Ohio

[73] Assignees: The Ohio States University, Columbus; The Cleveland Clinic Foundation, Cleveland, both of Ohio

[21] Appl. No.: 09/352,725

[22] Filed: Jul. 13, 1999

Related U.S. Application Data

[62] Division of application No. 08/806,596, Feb. 26, 1992, Pat. No. 5,968,820.

[51] Int. Cl.[7] .................................................. G01N 33/00
[52] U.S. Cl. ........................ 422/73; 435/325; 435/173.4; 435/2; 435/173.9; 435/286.5; 209/214; 209/216; 209/223.1; 209/231; 210/222; 210/223
[58] Field of Search ................................. 435/325, 173.4, 435/173.9, 2, 286.5; 422/73, 214, 216, 223.1, 231; 210/222, 223

[56] References Cited

U.S. PATENT DOCUMENTS

| | | |
|---|---|---|
| D. 384,415 | 9/1997 | Maloney et al. . |
| 2,056,426 | 10/1936 | Frantz . |
| 3,608,718 | 9/1971 | Aubrey, Jr. ................................ 209/214 |
| 4,663,029 | 5/1987 | Kelland et al. . |
| 4,961,841 | 10/1990 | Andres .......................................... 209/1 |
| 5,039,426 | 8/1991 | Giddings . |
| 5,049,540 | 9/1991 | Park et al. . |
| 5,053,344 | 10/1991 | Zborowski et al. . |
| 5,215,926 | 6/1993 | Etchells, III et al. . |
| 5,224,604 | 7/1993 | Duczmal et al. . |
| 5,240,856 | 8/1993 | Goffe et al. . |
| 5,378,624 | 1/1995 | Berenson et al. . |
| 5,465,849 | 11/1995 | Wada et al. . |
| 5,506,130 | 4/1996 | Peterson et al. . |
| 5,536,475 | 7/1996 | Moubayed et al. . |
| 5,541,072 | 7/1996 | Wang ....................................... 435/7.21 |
| 5,568,869 | 10/1996 | Turkenich ................................ 209/212 |
| 5,635,387 | 6/1997 | Fei et al. . |
| 5,672,481 | 9/1997 | Minshall et al. . |
| 5,684,712 | 11/1997 | Goffe et al. . |
| 5,695,989 | 12/1997 | Kalamasz . |

FOREIGN PATENT DOCUMENTS

3827252 A1   2/1990   Germany .

OTHER PUBLICATIONS

Zborowski M et al. Magnetic Flow Sorting Using a Model system of Human lymphocytes and a Colloidal Magnetic Label. Sep.–Oct. 1996, ASAIO Journal 42(5) M666–M671.

"Separation of Cells and Cell–Sized Particles by Continuous SPLITT Fractionation Using Hydrodynamic Lift Forces." Separation Science and Technology, 29(18), pp. 2493–2522, 1994.

"High Gradient Magnetic Separation of Cells on the Basis of Expression Levels of Cell Surface Antigens." Journal of Immunological Methods, 154 (1992) 245–252.

"Magnetic Flow Sorting Using a Model System of Human Lymphocytes and a Colloidal Magnetic Label." Maciej Zborowski, Lee R. Moore, Sridhar Reddy, Guo–Hua Chen, Liping Sun, and Jeffrey J. Chalmers. American Society for Artificial Internal Organs Journal 1996;42:M666–M671.

Primary Examiner—Jill Warden
Assistant Examiner—Huan Tran
Attorney, Agent, or Firm—Calfee, Halter & Griswold LLP

[57]   ABSTRACT

A method and apparatus for the fraction sorting of cells is provided. The invention include a dispensing device, aspirating device, flow channel and a magnetic assembly. A first fractional sorting device includes a dipole fractional cell sorter. The dipole fractional cell sorter includes large aspect ratio flow channel and a dipole magnetic assembly. A second fractional sorting device includes a quadrupole fractional cell sorter. The quadrupole fractional cell sorter includes an annular flow channel having inlet and outlet splitters, and a quadrupole magnetic assembly. The quadrupole magnetic assembly includes pole pieces having projecting members with convex surfaces and in is in physical communication with the annular flow chamber. The method of the present invention provides a flow through fractional cell sorting process which is based on the application of a magnetic force to cells having a range of magnetic labeling densities.

28 Claims, 7 Drawing Sheets

FRACTIONAL CELL SORTER

CROSS REFERENCE TO RELATED APPLICATIONS

This patent application is a divisional of Ser. No. 08/806,598 filed Feb. 26, 1997, now U.S. Pat. No. 5,968,820 titled "Fractional Cell Sorter."

Federal Sponsorship of this invention has been provided by Contract No. CA62349 awarded by the National Institutes of Health.

The invention relates generally to a device and method for sorting magnetically susceptible particles, and, more particularly, to a device and method for sorting cells having flow-through magnetic fractional cell separation. The invention further relates to a method of sorting and separating cells.

BACKGROUND OF THE INVENTION

Generally, cell sorting devices separate cell populations of interest from a suspension and/or other types of cells. The principal method of operation of early cell sorting devices relied on a cell's physical parameters to distinguish that cell from a suspension and/or other types of cells. Examples of bulk cell sorting techniques include filtration, which is based on cell size, and centrifugation, which is based on cell density. These techniques are effective as long as the cell population of interest is significantly different, with respect to size or density, from the suspension and/or the other cells in the population (i.e. a separation of red blood cells from blood.) However, when the cell population of interest does not differ significantly in size or density, the filtration and centrifugation techniques are ineffectual.

In attempting to address this problem, a technique was developed which did not rely on cell size or density differences relative to the suspension and/or the other cells in the population. This technique was based on the presence of a tagging element which was attached to the surface of the cell. This tagging technique has evolved to become a significant analytical tool in basic biological studies, applied biological studies, in the clinical diagnosis of diseases and the rapidly developing cell-based therapies in the treatment of diseases.

One application of this tagging technique is known as Fluorescence-Activated Cell Sorting (hereinafter FACS). In the FACS technique, an antibody-fluorescent label conjugate is used to tag a specific cell surface marker. The primary mode of operation of a FACS sorter is binary in nature, that is, it determines whether a cell has the threshold number of fluorescent labels (i.e. positive sorting) or it does not have the threshold number of fluorescent labels (i.e. negative sorting). This determination is made by passing cells, single file, through a device which can determine whether each cell includes the parameter of interest (e.g. fluorescence). The binary separation is determined by the setting of a threshold or "gate" (also sometimes called a trigger.) While the value of this "gate" or trigger is adjustable (i.e. quantitatively), the sorting process is still binary based on the threshold setting.

Furthermore, the rate of cell separation is relatively slow due to the fact that FACS sorters operate by examining a single cell at a time. Generally, a FACS sorter can provide a cell sorting rate of $10^3$ cells/second. Higher cell sorting rates are possible, however, these higher sorting rates may damage some cells. Still further, FACS sorters are relatively expensive and thus, most laboratory facilities are equipped with a limited number sorters.

Another technique employing cell tagging as a basis for separation is known as High Gradient Magnetic Separation (hereinafter HGMS). The concept of sorting materials based on their magnetic responsiveness was first introduced in the industrial and mining arts. These methods relied on the intrinsic magnetic properties of the sorted material (generally, iron (i.e. magnetic) from non-iron parts (i.e. non-magnetic)) as a basis of operation. See U.S. Pat. No. 2,056,426 issued to Frantz, "Magnetic Separation Method and Means," in 1936.

More particularly, in HGMS, a heterogeneous cell population, which includes a cell sub-population having magnetic cell tags, is passed through a magnetic field. As the heterogeneous cell population passes through the magnetic field, the cell sub-population labeled with the magnetic cell tags, becomes magnetically responsive to the applied magnetic field. That is, the cell sub-population including the magnetic tags will be subjected to a magnetic force which will cause the cells to be either attracted to (in the typical case), or repelled from, the magnetic field's source. Typically, the cell sub-population having the magnetic tags is attracted to the source of the magnetic field and collected by adhering to the magnetic source itself, or adhering to a cell collector device situated near the magnetic source. Therefore, the primary mode of the HGMS is also binary in nature, that is, it determines whether a cell has the magnetic tags or not.

The HGMS system, however, also has several drawbacks. Firstly, the cell sub-population of interest can be physically damaged during the HGMS process because of their forced magnetic massing at the collector device. Secondly, because the HGMS process sorts cells on the same fundamental principle as the FACS system, the HGMS method is also binary in nature. That is, both the FACS and HGMS systems separate cells based on the presence or absence of a parameter of interest (i.e. fluorescence and magnetic responsiveness, respectively).

While binary separation techniques are important, there is a desire in the biological sciences to fractionate cells in an "analog" fashion, that is, to sort cells based on the amount of tags bound to the cell. As mentioned above, binary cell sorting methods sort cells based on the presence or absence of a parameter of interest (i.e. magnetic responsiveness). Accordingly, it is an object of the present invention to provide a system and method for sorting cells based on the amount of tags bound to the cell.

SUMMARY OF THE INVENTION

According to the present invention, a apparatuses and methods are provided for fractionally sorting magnetically susceptible particles. A first method is provided for separating magnetically susceptible particles and includes the steps of fractionating a heterogeneous magnetically susceptible particle population while in a flow stream into fractionated flow streams by subjecting the heterogeneous magnetically susceptible particle population to a magnetic field. The step of fractionating a heterogeneous magnetically susceptible particle population while in a flow stream into fractionated flow streams further includes the steps: of generating flow compartments within the flow stream, controlling the flow rate of the flow stream, and/or generating efferent fractionated flow streams. The term "efferent" is defined as meaning bearing or conducting outward from a more central part. Moreover, the step of fractionating a heterogeneous magnetically susceptible particle population while in a flow stream into fractionated flow streams further includes the step of directing each fractionated flow stream into distinct outlet ports.

The present invention further provides a cell sorting device for the fractional sorting of cells and includes: a dispensing device for providing a sample flow and a carrier flow; a flow channel for allowing the flow of the sample and the carrier; a first interface device for interfacing the dispensing device to the flow channel, the first interface device including an inlet injector region; an aspirating device for aspirating the flow present in the flow channel; a second interface device for interfacing the flow channel to the aspirating device, the second interface device including an exit port region; and a magnetic assembly for creating a magnetic field. The magnetic assembly includes: a first and a second magnetic pole and an air gap disposed between the first and the second magnetic poles and configured to allow at least a partial insertion of the flow channel therein. The magnetic assembly is positioned substantially adjacent to the flow channel. Additionally, a fraction determining device for determining a sorted fraction distribution inside the flow channel is also provided.

The exit port region of the second interface device includes a plurality of collectors in a parallel, horizontal configuration. Similarly, the inlet injector region of the first interface device includes a plurality of inlet injectors in a parallel, horizontal configuration. The plurality of collectors are equally spaced from each other and the plurality of inlet injectors are also equally spaced from each other. The plurality of inlet injectors includes a sample injector and a plurality of carrier injectors. The sample injector includes a conical-shaped discharge chamber having a large height-to-base diameter ratio and is substantially longer than the carrier injectors. The plurality of collectors and the plurality of inlet injectors are further configured such that each collector and each inlet injector are within a flow compartment. The plurality of collectors and the plurality of inlet injectors may also be further configured such that each outlet injector has a common center line with an inlet injector. Additionally, the plurality of inlet injectors comprises a sample injector that is disposed between carrier injectors.

The flow channel includes a symmetrical cross-sectional geometry having a substantially uniform length and a substantially uniform width, wherein the length is substantially greater than the width. The flow channel is positioned within the magnetic field such that the vector direction of the magnetic forces created by the magnetic field are substantially parallel to the cross-sectional length of the flow channel.

A second method for fractionally sorting cells which is based on the density of a particular cell characteristic of interest is also provided by the present invention. The method includes the steps of: providing a flow channel having a symmetrical cross-sectional geometry that includes a substantially uniform length and a substantially uniform width, wherein the length is substantially greater and the width; magnetically labeling a cell population; injecting the magnetically labeled cell population into the flow channel at an area that is disposed between a first carrier injector area and a second carrier injector area; subjecting the magnetically labeled cell population in the flow channel to a magnetic field such that the vector direction of the magnetic forces therein is substantially parallel to the cross-sectional length of the flow channel. The step of injecting the magnetically labeled cell population into the flow channel at an area that is disposed between a first carrier injector area and a second carrier injector area includes the step of injecting the magnetically labeled cell population in an area which is interposed a predetermined distance from the length and width of the flow channel cross sectional geometry. The method further includes the step of controlling a flow of the magnetically labeled cell population and a carrier medium in the flow channel and controlling the magnetic susceptibility of the carrier medium.

The present invention also provides a second cell sorting device for the fractional sorting of cells. The device includes at least a first and a second stage. The first stage includes: a dispensing device for providing a sample flow and a carrier flow; a first stage flow channel for allowing the flow of the sample and the carrier; a first stage first interface device for interfacing the dispensing device to the flow channel; a first stage second interface device for interfacing the flow channel to the second stage; a first stage magnetic assembly for creating a magnetic field. The magnetic assembly including a first and a second magnetic pole and an air gap disposed between the first and the second magnetic poles and configured to allow at least a partial insertion of the first stage flow channel therein. The first interface device includes an inlet injector region and the second interface device includes an exit port region.

The second stage includes: a second stage flow channel for allowing the flow of the sample and the carrier; a second stage first interface device for interfacing the first stage to the second stage; a second stage second interface device for interfacing the flow channel to an aspirating device for aspirating the flow present in the flow channel; a second stage magnetic assembly for creating a magnetic field. The magnetic assembly including a first and a second magnetic pole and an air gap disposed between the first and the second magnetic poles and configured to allow at least a partial insertion of the second stage flow channel therein. The first interface device including an inlet injector region and the second interface device including an exit port region. The flow channel of the first and second stages includes a symmetrical cross-sectional geometry having a substantially uniform length and a substantially uniform width, wherein the length is substantially greater than the width. Further, the flow channel of the first and second stages is positioned within the magnetic field of each stage such that the vector direction of the magnetic forces created by the magnetic field of each stage is substantially parallel to the cross-sectional length of the flow channel of each stage. The cell sorting device for the fractional sorting of cells also includes a fraction determining device for determining a sorted fraction distribution.

The present invention also provides a third cell sorting device for the fractional sorting of cells. The device includes: a dispensing device for providing a sample flow and a carrier flow; an annular flow channel for allowing the flow of the sample and the carrier; the annular flow channel having an inlet and an outlet; a first annular splitter disposed at least partially within the inlet of the annular flow channel; a second annular splitter disposed at least partially within the outlet of the annular flow channel; an aspirating device for aspirating the flow present in the annular flow channel; and a magnetic assembly for creating a magnetic field.

The magnetic assembly includes: first, second, third and forth magnetic poles and an air gap disposed between the first, second, third and forth magnetic poles and configured to allow at least a partial insertion of the annular flow channel therein. Each magnetic pole comprises a projection member having a convex surface. The annular flow channel further comprises an outer and inner cylindrical wall and wherein the convex surface of each magnetic pole is in physical communication with the annular flow channel outer wall. The first, second, third and forth magnetic poles each further include a permanent magnet and a pole piece. The air gap includes a magnetic field having a magnetic force that includes a vector direction which is radially outward towards the annular flow channel outer wall. The annular flow channel further includes an inner wall and an annular separation region disposed between the inner and outer walls for allowing the migration of magnetically labeled cells.

The present invention also provides a fourth cell sorting device for the fractional sorting of cells. The device includes: a dispensing device for providing a sample flow and a carrier flow; an aspirating device for aspirating the flow present in the annular flow channel; at least a first and a second sorting stage for sorting a predetermined fraction of cells having a predetermined range of densities of a particular cell characteristic. The first and second sorting stages each include: an annular flow channel for allowing the flow of the sample and the carrier; the annular flow channel having an inlet and an outlet; a first annular splitter disposed at least partially within the inlet of the annular flow channel; a second annular splitter disposed at least partially within the outlet of the annular flow channel; and a magnetic assembly for creating a magnetic field. The magnetic assembly includes: first, second, third and forth magnetic poles and an air gap disposed between the first, second, third and forth magnetic poles and configured to allow at least a partial insertion of the annular flow channel therein. Each magnetic pole comprises a projection member having a convex surface.

The outlet of the annular flow channel of the first sorting stage includes a first fraction outlet port and the inlet port of the annular flow channel of the second stage includes a sample injection port. The first fraction outlet port of the first sorting stage are in fluid communication with the sample injection port of the second sorting stage. Each annular flow channel further includes: an outer wall; an inner wall; and an annular separation region disposed between the inner and outer walls for allowing the migration of magnetically labeled cells. The term fluid communication is hereby defined as any means, method or device allowing or providing for the flow of a fluid or fluids.

The present invention further provides a third method of fractionally sorting cells which is based on cell magnetization accomplished by tagging cells with suitable magnetic labels. The method including the step of providing an annular flow channel for allowing the flow of a magnetically labeled cell sample and a carrier; the annular flow channel having an inlet and an outlet, wherein the inlet comprises a sample injection area, a carrier injection area and an inlet annular splitter disposed therebetween; and wherein the outlet comprises a first sorted fraction output area, a second sorted fraction output area and an outlet annular splitter disposed therebetween. The method further includes the steps of: injecting magnetically labeled cells into the sample injection area; injecting a carrier into the carrier injection area; subjecting the magnetically labeled cells to a magnetic field having a magnetic force vector direction that is radially outward from the center of the annular flow channel; and collecting a first sorted fraction of cells and a second sorted fraction of cells. The method still further includes the step of controlling the flow of magnetically labeled cells and the carrier in the annular flow channel. The step of controlling the flow of magnetically labeled cells and the carrier in the annular flow channel includes the step of selecting a ratio of magnetically labeled cell flow rate to that of the carrier flow rate and/or the step of controlling the magnetic susceptibility of the carrier medium.

It is therefore an advantage of the present invention to provide a flow through, as opposed to batch, cell sorting method and device.

It is a further advantage of this invention to provide a cell sorting device and method which retains cell viability after the sorting process.

It is yet another advantage of the present invention to provide a device and method for high volume and high purity cell sorting.

It is yet another advantage of the present invention to provide to keep the tag cells suspended in a fluid stream as they flow through the separator.

It is still further another advantage of the present invention to provide a compact design that allows placement of the present invention in a controlled environment, such as a cold room.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENT

Before discussing the particulars of the present invention, a brief summary of the basic theory of paramagnetic separation will presented. In paramagnetic separation, the fundamental force being exploited for separation is the body force created between an induced paramagnetic label and an externally created magnetic field. This relationship is expressed in equation (1):

$$F_m = V\Delta\chi H \frac{dB}{dx} \qquad (1)$$

where $F_m$ is the magnetic force acting on the paramagnetic label, V is the volume of the label, $\Delta_\chi$ is the magnetic susceptibility of the label relative to a suspension medium, H is the magnetic field strength, and dB/dx is the magnetic field gradient (where field is measured as the magnetic induction, or the magnetic flux density, B). The above formula applies to the simplest, one-dimensional motion of the magnetic particle along an x axis, which also defines the direction of the field, and the field gradient.

The motion of large numbers of cells in a suspending medium can be conveniently expressed as the cell flux. Cell flux is defined as the number of cells crossing a unit surface area perpendicular to the motion of cells in unit time. The cell flux of magnetically-neutral cells is determined by the flow of the suspending medium. In the simplest case, in which there are no body forces acting on the cell, the flow is laminar and the cell dimensions are small, as compared to those of the flow channel. The cell flux equals the cell concentration (in units of cell number divided by unit volume) times the average flow velocity (in units of length divided by unit time) of the streamlines contacting the cell surface. Therefore, in the absence of body forces (such as gravity, magnetic or other), the flux of the magnetically-neutral cells follows flow streamlines.

The flux of the magnetically-labeled cells, in the presence of an outside, non-uniform magnetic field, is different from that of the magnetically-neutral cells. The difference in the direction (and magnitude) of the cell fluxes between the magnetically-labeled and non-magnetic cell populations in the flowing medium is an important concept upon which the operation of the present invention is based. The flux of the non-magnetic cells is governed by equation (2):

$$j^- = c^- v \qquad (2)$$

where $j^-$ is the flux vector of the non-magnetic (magnetically-negative) cells, $c^-$ is concentration of the non-magnetic cells, and v is the linear flow velocity vector. The flux of the magnetically-labeled cells is governed by equation (3):

$$j^+ = \alpha R c^+ \frac{V'\Delta\chi'}{3\mu_o \eta} \nabla B^2 + c^+ v \qquad (3)$$

where, $^+$ is the flux vector of the magnetic (magnetically-positive) cells, $c^+$ is the concentration of the magnetic cells, $\Delta_\chi'$ is the relative susceptibility of the magnetic reagent, V' is the volume of the magnetic reagent particle, $\alpha$ is the density of the magnetic reagent particles attached to a cell, R is the cell radius, $\mu_0$ is the magnetic permeability of free space (a constant), $\eta$ is the viscosity of the suspending liquid, and $\nabla B^2$ is the gradient of the magnetic flux density to the second power, which in the homogenous media, such as electrolyte solutions, is also a measure of the magnetic field energy density gradient.

A comparison of eqs. (2) and (3) shows that for a constant magnetic energy density, $\nabla B^2 = 0$ (representing the case of either the uniform magnetic field, or the case of no magnetic field), the direction of both vectors $j^-$ and $j^+$ is the same, and determined by the direction of vector v; in this case, both magnetic and non-magnetic fractions follow the same flow streamlines and, therefore, cannot be separated by the fluid flow. For the non-uniform spatial distribution of the magnetic field energy, $\nabla B^2 \neq 0$ in Eq.3, the flux of the magnetically-labeled cells, $j^+$, diverges from the flux of the non-magnetic cells, $j^-$, Eq.2. In this case, the magnetic cells cross the streamlines and move away from the non-magnetic cells, and thus both fractions can be separated by the flow.

The relative magnitude of the two expressions on the right side of Eq. (3) determines the performance of the magnetic flow separation. In general, the magnitudes of these two expressions should be comparable in order to maintain control over the magnetic and non-magnetic cell fluxes, as required by the magnetic flow sorting. The first, magnetic term of the right side of Eq. (3) predominates in applications of large, particulate magnetic labels (such as Dynabeads), and therefore such labels are preferable for batch-type (no flow) separations. The second, flow term of the right side of Eq. (3) predominates in applications of colloidal and molecular magnetic labels, which requires that the cell flux due to magnetic forces is directed perpendicular to the flow streamlines in order to maximize the magnetic separation effect.

Figure 1A:
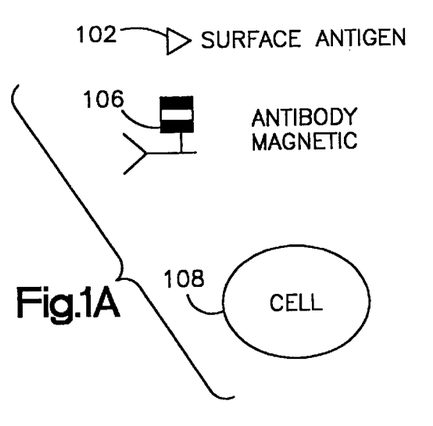
FIGS. 1A, 1B and 1C illustrate a cellular labeling complex which may be employed by the present invention.
Figure 1B:
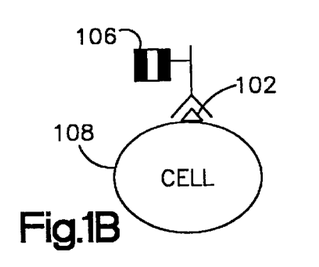
Figure 1C:
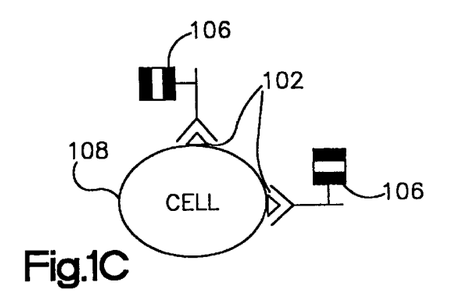

Referring now to FIGS. 1A, 1B and 1C, a cellular labeling complex of the present invention is shown. The cellular labeling complex includes a cell 108, a surface antigen 102 and magnetic antibody 106. The cell 108 includes surface antigen 102, e.g., proteins, which serve as a marker to which magnetic antibody 106 may be attached. FIG. 1B shows a cellular labeling complex including a single surface antigen or marker 102 and a single magnetic antibody 106. FIG. 1C shows a cellular labeling complex which includes a plurality of surface antigens 102 and a plurality of magnetic antibodies 106. Under ideal circumstances, each cell surface marker would include an antigen 102 and an antibody 106. In general, each cell has a characteristic density of cell surface marker $\alpha$. Assuming that the same amount of the magnetic reagent binds to each marker on the cell surface, the resulting magnetic force acting on the cell and the flux of the magnetically labeled cells (see Eq. (3)) are also proportional to $\alpha$.

Moreover, it should be noted that other cellular labeling complexes are possible. For example, one may attach a primary antibody—fluorescein conjugate to the surface marker and a secondary antibody—magnetic label conjugate to the primary antibody. The primary advantage of this cellular labeling complex is that it would allow additional analysis by FACS systems.

The magnetic antibody 106 may be of a plurality of types. More particularly, magnetic antibodies can be classified into three broad categories which are based on size: Particulate labels, Colloidal magnetic labels and Molecular magnetic labels.

Particulate labels are the largest in relative size to the other labels. One such well known particulate label is the Dynabead M450, manufactured by Dynal AG, Oslo, Norway. The Dynabead M450 is a monodisperse polystyrene bead which is doped with magnetite. It has a diameter of 4.5 $\mu$m and a magnetic susceptibility of $_{102}$ =0.245 (SI units).

Colloidal magnetic labels are smaller in size as compared to Particulate labels. One such well known colloidal magnetic label is the MACS microbead, manufactured by Miltenyi Biotec GmbH, Bergisch Gladbach, Germany. The MACS microbead is a dextran microbead doped with magnetite. It has a typical diameter of 50 nm.

Molecular magnetic labels are the smallest in terms of relative size. One well known molecular label is Ferritin. Ferritin is a ubiquitous iron storage protein with a typical diameter of 12 nm. While under the proper design specifications any of the three types of magnetic labels can be suitable, the illustrated embodiments employ either colloidal magnetic labels or molecular magnetic labels.

Moreover, cells may be rendered paramagnetic by binding a specific paramagnetic compound to a specific hapten on a cell or the specific or non-specific binding of a paramagnetic metal or metal complex directly to a cell (i.e., metal binding microorganism). Therefore, it should be apparent to those skilled in the art that a cell may rendered magnetic or paramagnetic in a variety of ways.

Figure 5:
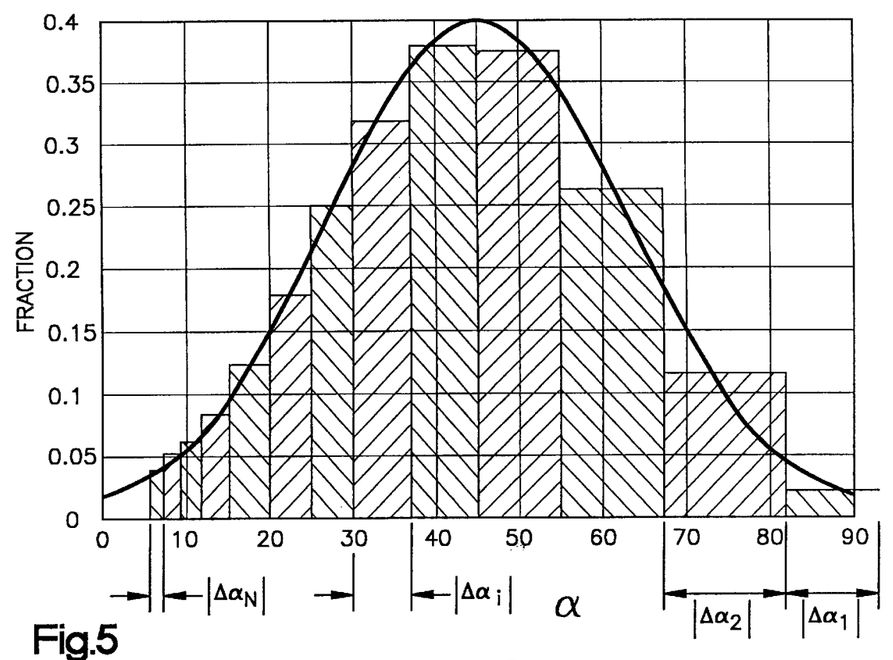
FIG. 5 is a graph showing a fractional distribution of a cell population having density, α, of a specific cell property of interest.

As was discussed above, the degree to which a magnetic marker binds to a cell may vary significantly in a given cell population. Illustrated in FIG. 5 is a graph showing a theoretical frequency (or fractional) distribution of a cell population (y-axis) with a density of the particular cell property of interest (x-axis). For example, this type of distribution is observed for the density of some specific cell surface receptors on human lymphocytes. Note that this distribution is similar to a normal distribution. Given this distribution in FIG. 5, and other relationships not herein discussed, it is possible to determine the number of "plates" required to achieve a desired level of fractional sorting via equation (4):

$$n = \frac{\ln\left(\frac{\alpha_n^*}{\alpha_0^*}\right)}{\ln\left[\frac{1+z\sigma}{1-z\sigma}\right]} = \frac{\ln\left[\frac{v_n^*}{v_0^*}\right]}{\ln\left[\frac{1+z\sigma}{1-z\sigma}\right]} \quad (4)$$

where the quantity $$(1-z\sigma) > 0 \quad (5)$$

It should be noted that, for the broadest application, this relationship has been non-dimensionalized such that $\alpha^*$, $v^*$ and $\sigma$ are non-dimensionalized with respect to a characteristic value for the system and the "1" in equation (5) arises from the non-dimensionalization of the cell diameter $D_c$, with respect to the mean diameter of the cell, $D_{cm}$. The introduction of $D_{cm}$, $\sigma$(the non-dimensionalized standard deviation of the cell diameter) and the z term reflects the observation that two cells, with the same $\alpha^*$, can have different magnetically induced velocities if they have different cell diameters. The degree to which a practitioner of the present invention wishes to include all of the cells with a given value of $\alpha^*$ is determined by the choice of z. For example, a value of 1 would include 68.27%, a value of 2 would include 95.45%, etc. The independent choice of z, along with the cell defined values of $\sigma$, $\alpha^*_0$ and $\alpha^*_n$ (or, alternatively, $v^*_0$ and $v^*_n$) determines the number of "plates" or stages of cell sorting. For example, binary separation consists of two "plates" in that, either the cell has the specific property of interest $\alpha^*$, or it does not. It should be further noted that, for the purpose of clarity, not all of the "plates" or "stages" have been illustrated in FIG. 5.

Another important concept, related to equation (4), is the range of velocities that can be obtained as a result of this distribution in cell diameters as discussed above. For a specific value of $\alpha^*$, a range of velocities can be obtained, and this range is represented by equation (6):

$$\frac{Mg\alpha^* F_b^*}{9}(1-z\sigma) < v_c^* \le \frac{Mg\alpha^* F_b^*}{9}(1+z\sigma) \quad (6)$$

Where Mg is the ratio of magnetic to drag forces and $F_b^*$ is the non-dimensional magnetic force acting on one magnetic label. This range of velocities can be represented by equation (7):

$$|\Delta v_c^*| = Mg\frac{\alpha F_b}{9} 2z\sigma \quad (7)$$

This "spread," or "range" of cell velocities due to the distribution of cell diameters is analogous to the "height" of a theoretical "plate" as discussed in the distillation and chromatography arts.

Equally, it can be shown that the differential cell densities, $\alpha^*$, between cells with the same velocity, $v_c^*$, as a result of the distribution of cell diameters, can be described by equation (8):

$$|\Delta \alpha^*| = \frac{v_c^* 9}{F_b^* Mg}\left[\frac{2z\sigma}{1-z^2\sigma^2}\right] \quad (8)$$

A principal design criteria of the dipole and quadrupole fractional cell sorters of the present invention is that a range of densities of a specific cell characteristic $|\Delta\alpha^*|$ of interest may be removed by each "plate" or "stage" of the sorter. In the case of the dipole fractional cell sorter of the present invention, each "plate" or "stage" refers to a flow compartment, to be presently described, that is defined by a plurality of boundary streamlines. In the case of the quadrupole fractional cell sorter, each "plate" or "stage" also refers to a flow compartment, to be presently discussed, which is also defined by a plurality of boundary streamlines. Therefore, each fractional cell sorter of the present invention may be designed such that cells with a range of densities $|\Delta\alpha^*|$, as defined by equation (8), are within a "stage" for a sufficiently long time so that the cells may migrate away from the stream which would maintain them in their present "stage", or the exit stream of the current "stage."

Dipole Magnetic Sorter

Figure 2:
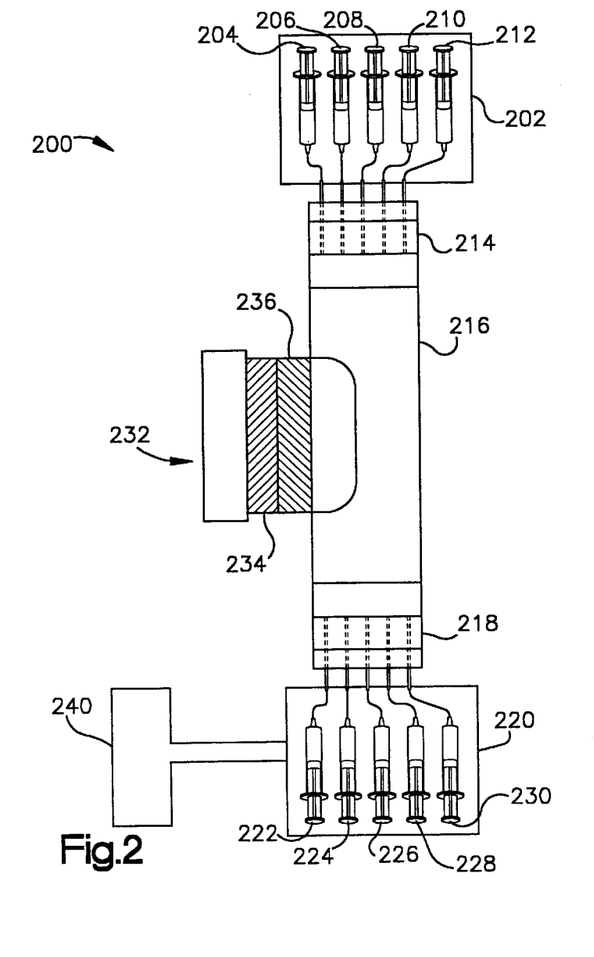
FIG. 2 is a block diagram illustrating certain components of a dipole fractional cell sorting device of the present invention.

Referring now to FIG. 2, a dipole magnetic sorter 200 of the present invention is shown which performs fractional cell sorting. To recall, fractional cell sorting, or analog sorting, separates cells based on their cell surface marker density (e.g. magnetic label density). A discussion of the dipole magnetic sorter 200 components and their function will be presented first, followed by an operational description of the sorter.

In particular, the dipole magnet sorter 200 of the present invention includes a dispensing device 202, a dispenser-channel interface device 214, a flow channel 216, a channel-aspirator interface device 218, an aspirator device 220 and a magnet device 232. The dispensing device 202 and the aspirating device 220 are for providing precisely controlled flow through the dipole magnetic sorter 200. While any device(s) which provide the ability to precisely control flow may be used for the dispensing device 202 and the aspirating device 220, the illustrated embodiment employs two identical multi-syringe pumps operating in infuse and refill modes to control flow. The dispensing device 202 includes five dispensing syringes 204–212 and the aspirating device 220 includes five aspirating syringes 222–230. In the illustrated embodiment, dispensing syringe 210 includes a cell population to be sorted and dispensing syringes 204, 206, 208 and 212 include carrier or suspension mediums. It should be noted, however, that other configurations, based on the teachings herein, of dispensing syringe contents will be apparent to those skilled in the art. For example, dispensing syringe 208 may include the cell population to be sorted and the remaining dispensing syringes 204, 206, 210 and 212 may include the carrier or suspension medium. A fraction determining device 240 for determining a sorted fraction distribution inside the flow channel is also provided. The fraction determining device 240 may be a FACS or other similar type device for precisely determining the distribution of sorted fractions.

The dispenser-channel interface device 214 and the channel-aspirator interface device 218 are of similar construction. The dispenser-channel interface device 214 includes five holes through which injectors are inserted. These holes and their spatial configuration are important in defining flow compartments and boundary streams, to be presently discussed. The injectors are channels through which the cell population(s) and suspension medium(s) must pass through before entering the flow channel 216. The dispensing device 202 is in flow communication with the dispenser-channel interface device 214 via a plurality tubing devices. In the illustrated embodiment, the tubing devices are Teflon tubing having an inner diameter of 0.78 mm. The channel-aspirator interface device 218 is of similar construction and includes five evenly spaced holes through which collectors are also inserted. It will be apparent to those skilled in the art that the holes and collectors need not be evenly spaced, as will be presently discussed.

The sample injector 210 and a portion of the dispenser-channel interface device 214 to which it is connected, are modified as compared to the carrier injectors 204–208 and 212 and their corresponding portions on the dispenser-channel interface device 214. The sample injector 210 and the portion of the dispenser-channel interface device 214 to which it is connected include an inverted, conical-shaped chamber of a large height-to-base diameter ratio, with the cone-end diameter discharging the sample directly into the dispenser-channel interface device 214. The tubing providing the sample flow into the flow channel 216 is significantly extended as compared to the tubing providing the carrier medium flow into the flow channel 216. These modifications serve two purposes. First, they prevent cell loss due to gravitational sedimentation on the substantially horizontal bottom portions of the syringes of the dispensing device 202 and the dispenser-channel interface device 214. Second, they provide for the injection of the sample into a fully-developed flow stream of the carrier medium.

The aspirating device 220 is also in flow communication with the channel-aspirator interface device 218 via a plurality of tubing devices. The dispenser-channel interface device 214 and the channel-aspirator interface device 218 are in flow communication with the flow channel 216 such that the injectors may provide fluid flow into the flow channel 216. The flow channel 216 includes a large aspect ratio, rectangular glass channel. In the illustrated embodiment, the large aspect ratio, rectangular glass channel has the following dimensions 1 mm×15 mm×150 mm (i.e., height×width×length.) A magnet assembly 232 is provided for producing a magnetic field and is placed in close physical proximity to the flow channel 216. The magnet assembly 232 includes two pairs of magnets 234 and 236, at least two pole pieces and an interpolar air gap. In the illustrated embodiment, the two pairs of magnets 234 and 236 are neodymium-iron-boron permanent magnets producing flux densities of approximately 1.5 Tesla in the interpolar air gap. The physical dimensions of the magnets are approximately 0.5"×2.0"×2.0". The pole pieces are made of soft iron or other suitable material which can efficiently circuit a magnetic flux. It should be apparent to those skilled in the art that electromagnets may also be employed instead of or in combination with permanent magnets.

Figure 3:
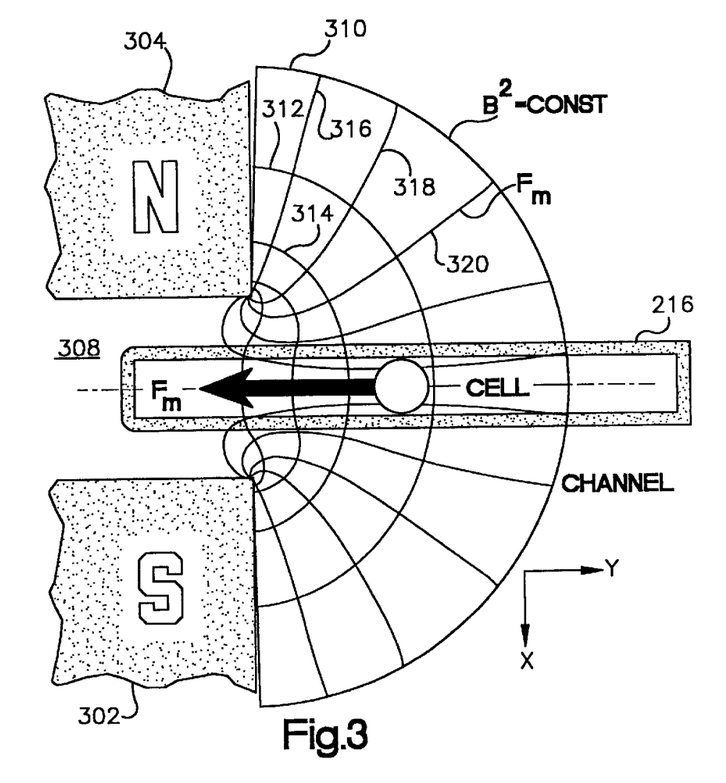
FIG. 3 is a plan view of the dipole fractional cell sorting device of the present invention illustrating certain components of the dipole fractional cell sorting device and its associated magnetic field characteristics.

Referring now to FIG. 3, a plan view of the dipole separator 200 of the present invention is shown. More particularly, illustrated in the plan view of FIG. 3 are the physical locations of pole pieces 302 and 304. The pole pieces 302 and 304 are of opposite polarity. In between the pole pieces 302 and 304 is an interpolar air gap 308. The interpolar air gap 308 is dimensioned so as to allow at least a partial insertion of the flow channel 216 therein. Also illustrated in FIG. 3 are the constant energy density lines $B^2$ (310, 312 and 314, for example) and the force lines $F_m$ (316, 318 and 320, for example). In the illustrated embodiment, the flow channel 216 is at least partially inserted into the interpolar air gap 308 and is position therein such that the constant force lines Fm create a predominant direction of magnetic force that is towards the magnet. Therefore, a cell that has been marked with a magnetic label will be subjected to a force $F_m$ having a direction as shown in FIG. 3.

Figure 4:
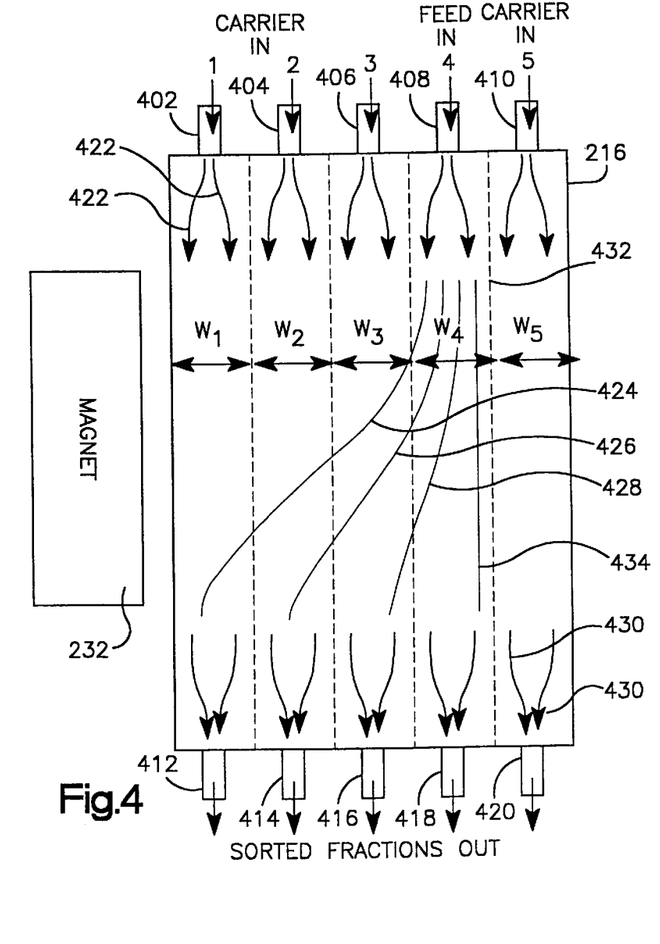
FIG. 4 is an illustration of the operation characteristics of the dipole fractional cell sorter of the present invention.

FIG. 4 illustrates the operation characteristics of the dipole fractional cell sorter of the present invention. More specifically, shown in FIG. 4 is the flow channel 216, dispenser-channel injectors 402–410, channel-aspirator collectors 412–420, magnetic assembly 232 and the cell trajectories 424–428 and 434. Injector 408 is the feed in injector that includes the cell population or sub-population to be fractionally sorted. Injectors 402, 404, 406 and 410 are carrier injectors and include a carrier medium or suspension. The magnetic assembly 232 is positioned to the left of the flow channel 216, as shown. The collectors 412–420 will, sometimes hereinafter, be referred to as the exit ports and include the sorted fractions of the cell population or sub-population.

In operation, a carrier medium is injected through injectors 402–406 and 410 into the flow channel 216. A distribution of flow rates between injectors 402 through 410 establishes a distribution of inlet streamlines 422 inside the flow channel 216. In particular, it establishes the positions of boundary inlet streamlines which separate fluid flows that originate from different injectors. The inlet boundary streamlines are indicated by broken lines, such as reference number 432, for example. The outlet flows 430 are collected by outlet collectors 412–420 at the bottom of the flow channel 216. The distribution of flow rates between outlet collectors 412–420 establishes a distribution of outlet flow streamlines 430 inside the flow channel 216. In particular, they establish the positions of boundary outlet streamlines that separate fluid flows terminating in different collectors. In general, the positions of the inlet boundary streamlines may not coincide with the positions of the outlet boundary outlet streamlines. In the illustrated embodiment shown in FIG. 4, the inlet and outlet boundary streamlines coincide and are shown by broken lines at 432, for example. The width of the flow compartments created by the streamlines is determined by the positions of the streamlines, as indicated by $W_1$, $W_2$, $W_3$, $W_4$, and $W_5$.

The cell suspension, containing a mixture of magnetically-labeled and unlabeled cells, is pumped into the inlet injector 408, and into the flow compartment identified by width $W_4$. The un-labeled, non-magnetic cells follow the streamlines of the flow compartment $W_4$, shown illustratively at 422, and are collected at the outlet port 418. The magnetically-labeled cells cross streamlines as they travel towards the source of the magnetic energy gradient 232, and given sufficient time, traverse the boundary streamline separating flow compartment $W_4$ from the adjacent flow compartment $W_3$. In general, the magnetically-labeled cells may have different magnetizations due to differential binding of the magnetic labels to the cells, as discussed above. Therefore, one may expect that the magnetic cells travel at different velocities towards the magnet: those cells that bind the largest amount of the magnetic label will travel the fastest across the streamlines, while those cells that bind a small amount of magnetic label will travel more slowly. Under suitable flow conditions, the cells having a large density of magnetic labels traverse all three boundary streamlines separating flow compartment $W_4$ from the flow compartment $W_1$, and are collected at the outlet injector 412. This cell trajectory is indicated at 424. The cells with smaller densities of magnetic labels are distributed between flow compartments $W_2$ and $W_3$, as indicated by streamlines 426 and 428, respectively. As a result of the operation of the dipole fractional cell sorter 200 of the present invention, the magnetic cells are collected as fractions 1 through 3 in the order of decreasing cell magnetization; non-magnetic cells are collected as fraction 4.

An important feature of the dipole fractional cell sorter of the present invention is the ability to manipulate the sorted fractions 1 through 4 by manipulating the positions of the boundary streamlines (shown as 432, for example). In particular, one may focus the stream of the cells entering the flow channel 216 by selecting a small width "w4" of the respective flow channel $W_4$ by the suitable selection of a large flow rate ratio of the carrier medium to the sample feed at the inlet injectors 402–410. Such focusing of the feed sample stream may be desirable in order to avoid the contamination of the magnetic cells by the non-magnetic cells in fractions 1 through 3, and thus would result in highly specific enrichment of the medium to high-magnetic cells in fractions 1 through 3 with possible losses of low-magnetic cells in fraction 4. One may also de-focus the stream of the cells entering the flow channel by selecting a large width "w4" of the respective flow channel $W_4$ by suitable selection of small flow rate ratio of the carrier medium to the sample feed at the inlet injectors 402–410. Such de-focusing of the feed sample stream may be desirable in order to avoid the contamination of the non-magnetic cells by the magnetic cells in fraction 4, and thus would result in highly specific depletion of the magnetic cells from fraction 4 with possible losses of the non-magnetic cells in fractions 3 (and possibly 2 and even 1). One may further manipulate the sorted fractions 1 through 4 by manipulating the inlet boundary streamlines, outlet boundary streamlines, or both, independently. The ability to control the positions of the inlet and outlet boundary streamlines leads to the exact control of the distribution of the magnetic cells in fraction 1 through 4 according to cell magnetization.

It is further possible to sort or remove a range of densities of a specific cell characteristic (e.g. magnetic susceptibility) by a dipole fractional sorter device which includes a plurality of stages. A multi-stage dipole fractional cell sorter device of the present invention includes at least a first and a second stage. The first stage includes: a dispensing device for providing a sample flow and a carrier flow; a first stage flow channel for allowing the flow of the sample and the carrier; a first stage first interface device for interfacing the dispensing device to the flow channel; a first stage second interface device for interfacing the flow channel to the second stage; a first stage magnetic assembly for creating a magnetic field. The magnetic assembly includes a first and a second magnetic pole and an air gap disposed between the first and the second magnetic poles and configured to allow at least a partial insertion of the first stage flow channel therein. The first interface device includes an inlet injector region and the second interface device includes an exit port region.

The second stage of the multi-stage dipole fractional cell sorter includes: a second stage flow channel for allowing the flow of the sample and the carrier; a second stage first interface device for interfacing the first stage to the second stage; a second stage second interface device for interfacing the flow channel to an aspirating device for aspirating the flow present in the flow channel; a second stage magnetic assembly for creating a magnetic field. The magnetic assembly including a first and a second magnetic pole and an air gap disposed between the first and the second magnetic poles and configured to allow at least a partial insertion of the second stage flow channel therein. The first interface device including an inlet injector region and the second interface device including an exit port region.

The flow channel of the first and second stages includes a symmetrical cross-sectional geometry having a substantially uniform length and a substantially uniform width, wherein the length is substantially greater than the width. Further, the flow channel of the first and second stages is positioned within the magnetic field of each stage such that the vector direction of the magnetic forces created by the magnetic field of each stage is substantially parallel to the cross-sectional length of the flow channel of each stage. The multi-stage cell sorting device also includes a fraction determining device for determining a sorted fraction distribution.

The first stage second interface device includes a plurality of collectors in its exit port region and the second stage first interface device includes a plurality of injectors in its inlet injector region. Flow communication between the two stages is established by flowably connecting one collector of the first stage second interface device to sample injector of the second stage first interface device. Moreover, it is possible to have N stages, where N is any integer greater than one, in the multi-stage dipole fractional cell sorter with the ultimate number being dependent on design criteria.

In order to more fully understand the dipole fractional cell sorter 200 of the present invention, an illustrative example of the operation of the preferred embodiment on a cytotoxic T lymphocyte cell population may be useful. The cytotoxic T lymphocyte cells, which are characterized by the presence of a CD8 surface marker, were tagged with magnetic labels in preparation of sorting. The carrier fluid was composed of phosphate-buffered saline at a physiological concentration of 0.15 mol. per liter and bovine albumin at a concentration of 3 grams per 100 ml. The same fluid medium was used for suspending the cells in the sample. The magnetically label CD8 cells were then placed in the dipole fractional sorter 200 of the present invention, where the saturation magnetization inside the interpolar air gap 308 was $B_0$=1.344 Tesla and the maximum value of the magnetic field gradient, in the plane of symmetry of the interpolar air gap, was 0.261 T/mm. The mean carrier flow velocity was 0.2 mm/s and the mean effective cell volumetric magnetic susceptibility $\Delta_\chi$ was $20 \times 10^{-6}$ in SI units. As shown in FIG. 4, the trajectories of the magnetically labeled CD8 cells was in the general direction of the magnetic assembly 232. A high purity of CD8 cells, defined as the ratio of CD8 cells to the total number of cells in the sample, was achieved Quadrupole fractional cell sorter:

A quadrupole fractional cell sorter of the present invention will now be described. The principle of operation of the quadrupole fractional cell sorter is fundamentally the same as the previously described dipole fractional cell sorter. Namely, the fundamental force being exploited for separation is the body force created between an induced paramagnetic, or magnetic, label and an externally created magnetic field. This relationship was described above in equation (1). Additionally, the above discussion relating to cellular labeling complexes and magnetic antibodies in the case of the dipole magnetic sorter is equally applicable to the present discussion of the quadrupole fractional cell sorter and therefore will not be repeated.

A principal design criteria of the quadrupole fractional cell sorter of the present invention is that a range of densities of a specific cell characteristics $|\Delta\alpha^*|$ of interest should be removed by each "plate" or "stage" of the sorter. This is accomplished by designing the quadrupole fractional cell sorter such that cells with a range of densities $|\Delta\alpha^*|$, as defined by equation (4), are within a "stage" for a sufficiently long enough time so that the cells may migrate away from the stream which would carry them into a next "stage", or the exit stream of the current "stage."

Figure 6:
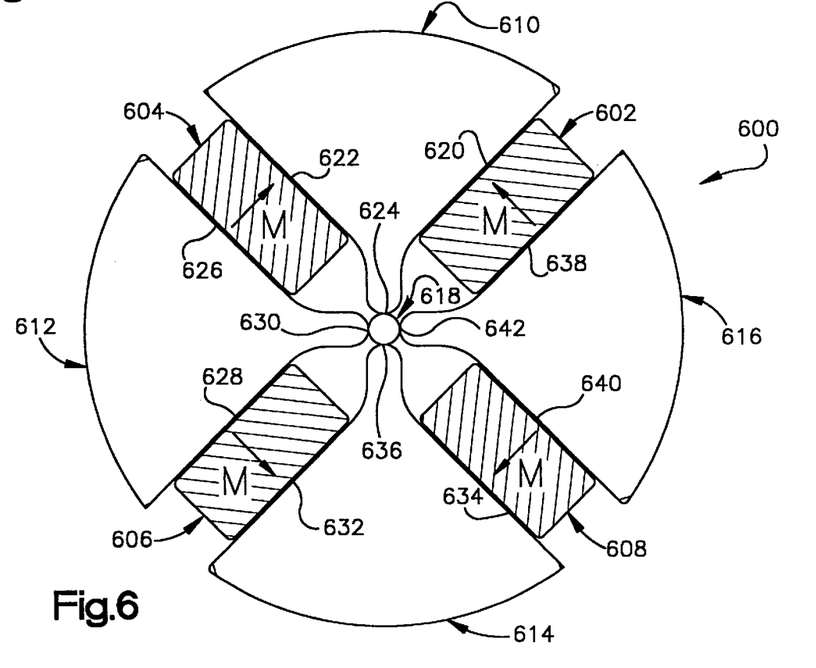
FIG. 6 is a cross-sectional top view of a single "plate" or "stage" of a quadrupole fractional cell sorter of the present invention.

Referring now to FIG. 6, a cross-sectional top view of a single "plate" or "stage" 600 of a quadrupole fractional cell sorter of the present invention is shown. The stage 600 includes permanent magnets 602–608, pole pieces 610–616 and a cylindrical flow assembly 618. The permanent magnets 602–608 are block-like in nature with flat outer surfaces that intersect each other at 90 degree angles. The direction of magnetization of each permanent magnet 602–608 is indicated in FIG. 6 via an arrow labeled M. While the surfaces of the pole pieces 610–616 and permanent magnets 602–608 have been shown as having rectangular geometries, their surfaces may employ curved features which would, in turn, affect the maximum value and spatial distribution of the magnetic forces inside the flow channel. It should be apparent to those skilled in the art that electromagnets may also be employed.

The pole pieces 610–616 are constructed such that a permanent magnet is situated between each pole piece as shown in FIG. 6. More particularly, pole piece 610 includes flat surfaces 620 and 622 which are placed in close proximity to, or in physical contact with, permanent magnets 602 and 604 respectively. Pole piece 610 also includes a projection member having a convex surface 624. Pole pieces 612–616 are similarly constructed. Specifically, pole piece 612 includes flat surfaces 626 and 628 and a projection member having a convex surface 630. Pole piece 614 includes flat surfaces 632 and 634 and a projection member having a convex surface 636. Pole piece 616 includes flat surfaces 638 and 640 and a projection member having a convex surface 642. The convex surfaces 624, 630, 636 and 642 are positioned such that they are in close proximity to, or in physical contact with, cylindrical flow assembly 618.

Figure 7:
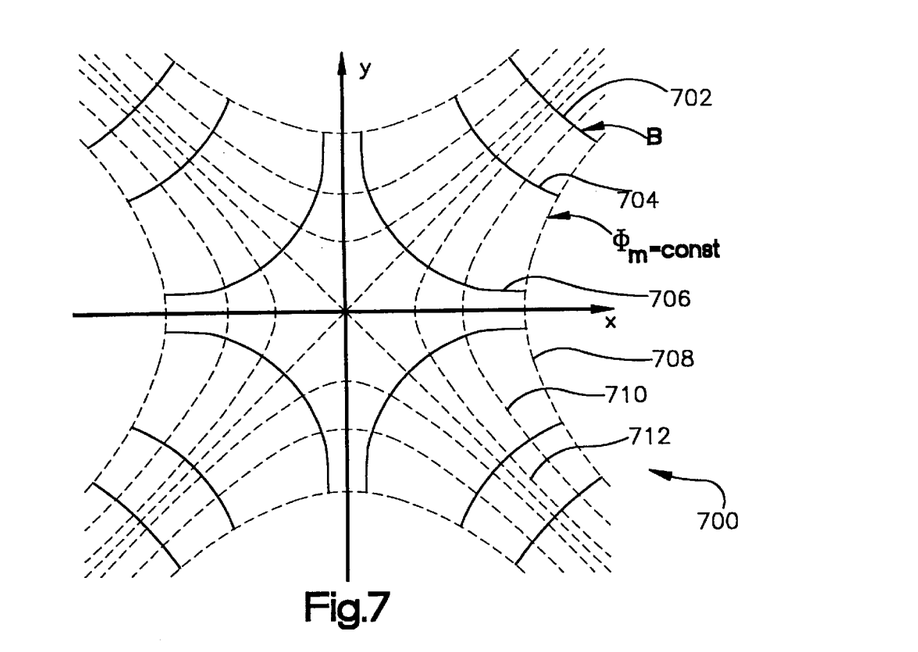
FIG. 7 is a plot of the quadrupole magnet field generated by the quadrupole fractional cell sorter stage of FIG. 6.

Illustrated in FIG. 7 is a plot 700 of the quadrupole magnet field generated by the is stage 600 of FIG. 6. Specifically, FIG. 7 shows the magnetic field flux density lines B (702, 704 and 706, for example) and the equipotential magnetic field lines $\Phi_m$ (708, 710 and 712, for example). The quadrupole magnet field illustrated in FIG. 7 is defined by a linear dependence of the magnetic field flux density B on a radial coordinate system. It can be shown that the magnetic force acting on a magnetic dipole in the quadrupole magnetic field is defined by equations (7) and (8).

$$B = B_0 r' \quad (7)$$

$$F_m = \frac{V \Delta \chi}{\mu_0} \frac{B_0^2}{r_0} r' \quad (8)$$

Figure 8:
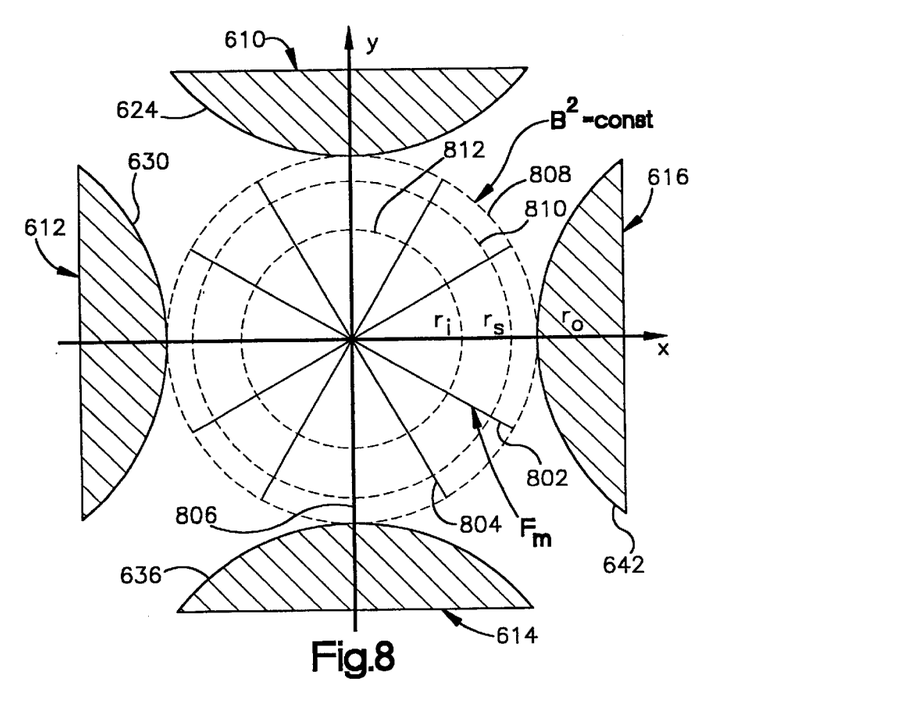
FIG. 8 is a plot of the magnetic force lines $F_m$ and the constant energy density lines $B^2$ which are generated by the quadrupole magnetic field of the present invention.

In equations (7) and (8), $r_0$ is the radius of the annular cylindrical flow assembly outer wall (FIG. 8), $r'=r/r_0$ and $B_0$ determines the magnetic flux density at $r'=1$. FIG. 8 illustrates the magnetic force lines $F_m$ (802, 804 and 806, for example), the constant energy density lines $B^2$ (808, 810 and 812, for example), the convex surfaces 624, 630, 636 and 642 of pole pieces 610, 612, 614 and 616, respectively. As in equation (1), V is the volume of the magnetic dipole label and $\Delta_\chi$ is the magnetic susceptibility of the label relative to the suspension medium.

The radial migration of magnetically labeled cells in the quadrupole magnetic field, along the force lines, as defined by equation (8), defines the quadrupole fractional cell sorter geometry of the present invention. The preferred geometry is that of a cylindrical flow assembly 618 having a thin annulus placed in physical communication with the convex pole piece surfaces 624, 630, 636 and 642 (all shown in FIG. 6). The discussion following equations (2) and (3) above relating to the sorting of magnetically labeled cells from non-magnetic cells in a flowing medium is also applicable in the present case. One may obtain an explicit dependency of the magnetically labeled cell flux on based on a cell's radial position by inserting equation (7) into equation (3).

Figure 9:
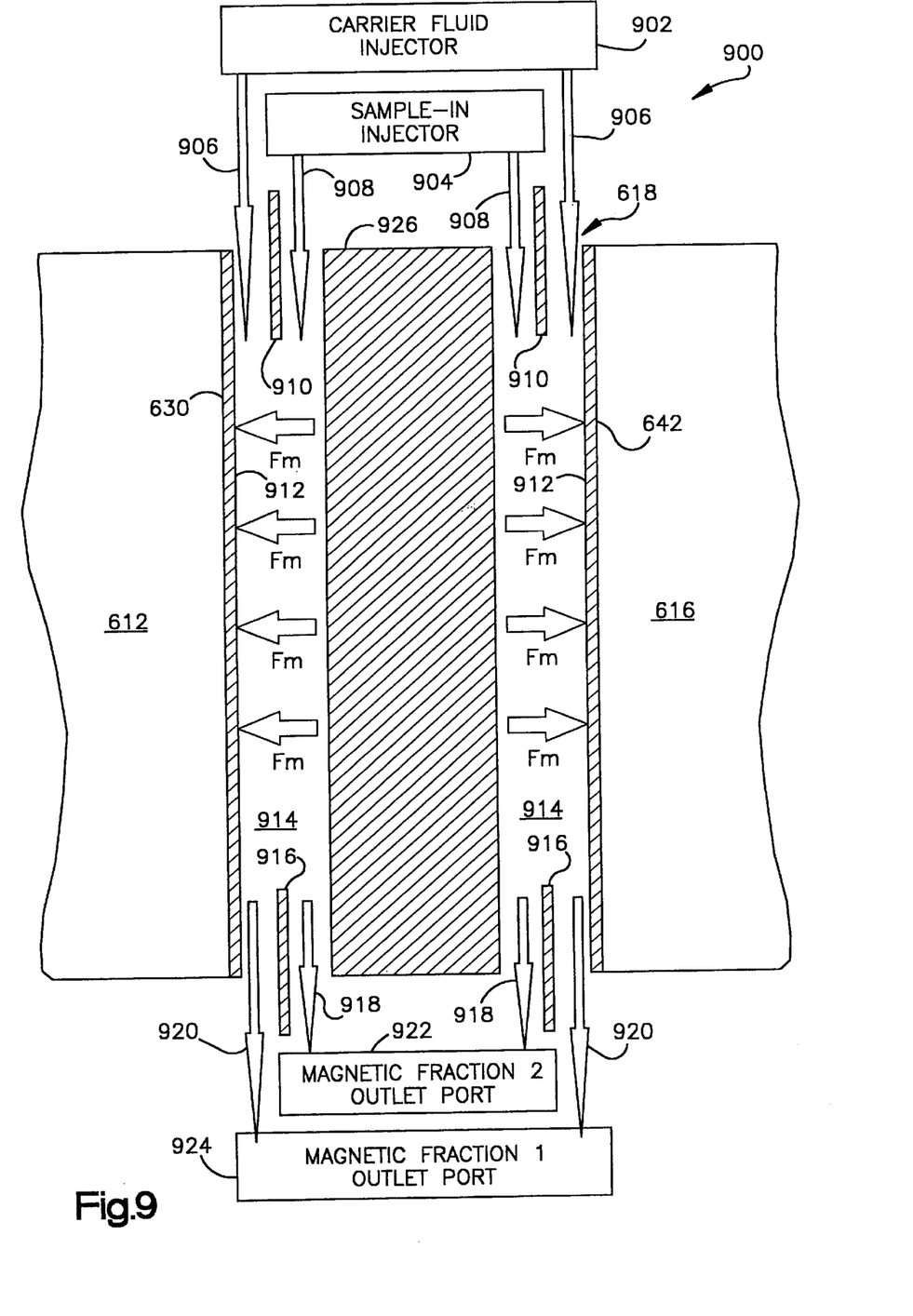
FIG. 9 is an elevated, cross-sectional view of the cylindrical flow assembly of a quadrupole fractional cell sorter stage of the present invention.

Illustrated in FIG. 9 is an elevated, cross-sectional view of the cylindrical flow assembly 618 and certain other components of the present invention. The cylindrical flow assembly 618 includes an annulus 912, cylindrical flow splitters 910 and 916 at the cylindrical flow assembly's inlet and outlet ends of the annulus 912, an annular separation region 914 and an inner cylindrical rod 926. Also shown are pole pieces 612 and 616, with their associated convex surfaces 630 and 642, respectively, a carrier fluid injector 902, a sample-in injector 904, a magnetic fraction 1 outlet port 924 and a magnetic fraction 2 outlet port 922.

In operation, the sample-in injector injects a sample 908, which includes the cell population or sub-population to be sorted, into an annular space between the cylindrical flow splitter 910 and the inner cylindrical rod 926. The carrier fluid injector 902 injects a carrier fluid, or suspension, 906 into an annular space between the annulus wall 912 and the cylindrical flow splitter 910. The sample 908 and carrier 906 will flow from their injector regions into annular separation region 914. In annular separation region 914, a radial migration of magnetically labeled cells occurs. More particularly, magnetically labeled cells in the sample 908 are subjected to force $F_m$ which has a vector direction as shown (i.e., radially outwards toward the annulus 912.) Cell separation is achieved by the differential radial migration of the magnetically labeled cells. Specifically, the magnetically labeled cells migrate in an outward direction toward the annulus 912 while he un-labeled cells remain in the original flow stream of sample 908 (i.e., close proximity to the outer surface of cylindrical rod 926).

Given sufficient time in annular separation region 914, the magnetically labeled cells sufficiently displace towards the annulus wall 912. The amount of time a cell, or cells, are in the annular separation region 914 is primarily dictated by, among other things, the physical length of the annular separation region 914 and/or the cell velocity. Once the cells have been in the annular separation region 914 for a sufficiently long enough time so that a radial migration of magnetically labeled cells has occurred, cylindrical flow splitter 916 splits the flow into a first magnetic fraction 920 and a second magnetic fraction 918. The first magnetic fraction 920 exits the cylindrical flow assembly 618 via an annular space between the annulus wall 912 and the cylindrical flow splitter 916 and enters an outlet port 924. The second magnetic fraction 918 (which can include magnetic and non-magnetic cells) exits the cylindrical flow assembly 618 via an annular space between the cylindrical flow splitter 916 and the inner cylindrical rod 926 and, thereafter, enters an outlet port 922. In the case of binary sorting where it is desired to sort magnetically labeled cells from non-magnetic cells, the first magnetic fraction 920 would include the magnetically labeled cells and the second magnetic fraction 918 would include the non-magnetic, or un-labeled, cells.

Figure 10:
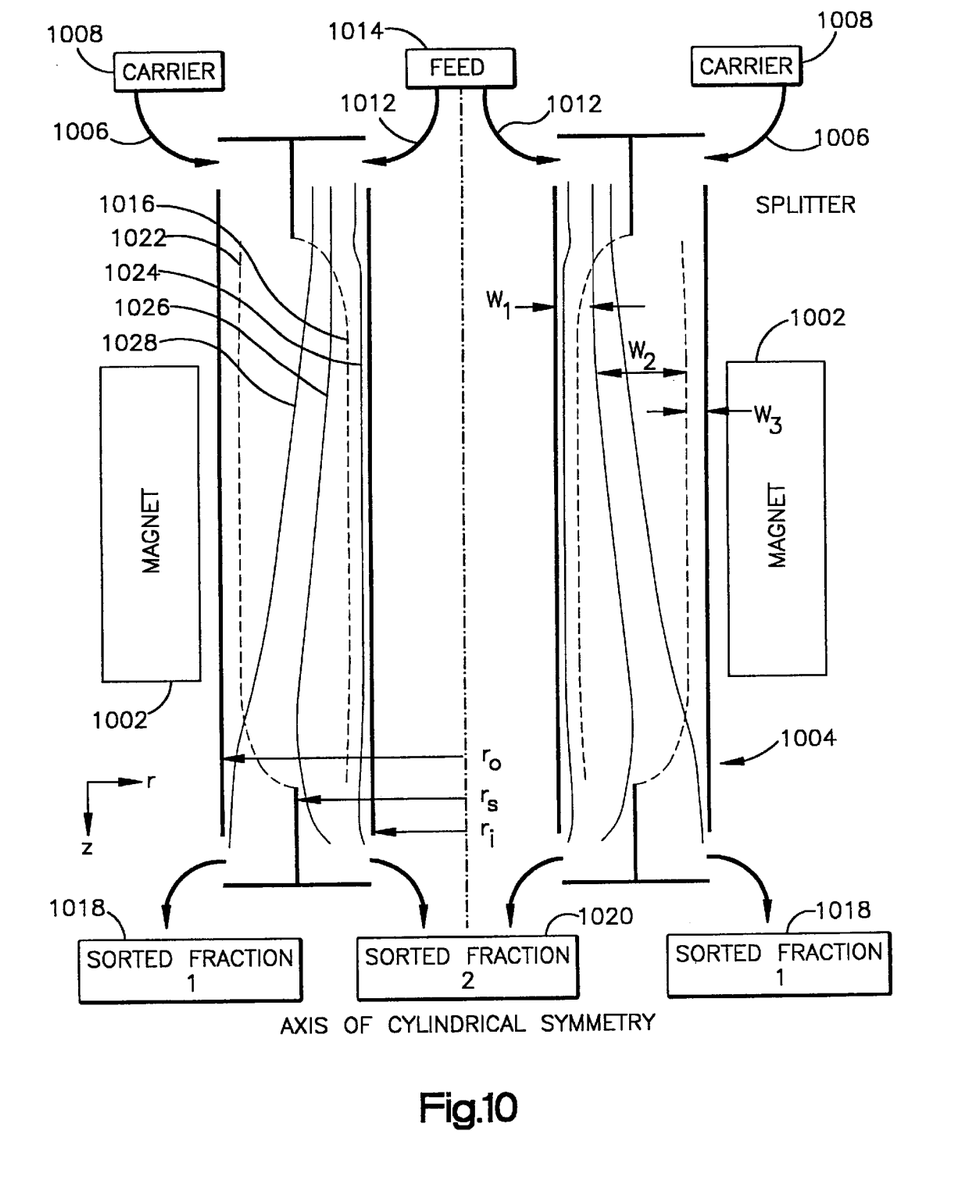
FIG. 10 illustrates a schematic axial cut, along the axis of symmetry of a single stage of a quadrupole fractional cell sorter of the present invention.

The principle of operation and other characteristics of the quadrupole fractional cell sorter of the present invention are further illustrated in FIG. 10. FIG. 10 shows a schematic axial cut, along the axis of symmetry of a single stage of a quadrupole fractional cell sorter of the present invention. The source of the magnetic energy gradient 1002 is positioned around the annular flow channel 1004. A carrier medium 1006 is pumped into an inlet port 1008. The cell sample 1012 is pumped into inlet port 1014. The distribution of flow rates between inlet ports 1008 and 1014 establishes a distribution of inlet streamlines inside the annular flow channel 1004. In particular, this distribution of flow rates establishes the position of the boundary inlet streamline 1016 that separates the fluid flow originating in inlet port 1014 from that originating in inlet port 1008. The outlet flow is collected in two outlet ports 1018 and 1020 at the bottom of the annular flow channel 1004. The distribution of flow rates between outlet ports 1018 and 1020 establishes the distribution of outlet flow streamlines inside the flow channel 1004. In particular, it establishes the position of the boundary outlet streamline 1022 that separates the fluid flows terminating in the 1018 and 1020 outlet ports. In general, the positions of the inlet boundary streamlines may not coincide with the positions of the boundary outlet streamlines, as shown in FIG. 10. The width of the flow compartments is determined by the positions of boundary streamlines 1022 and 1016 and the annular flow chamber 1004 dimensions, and are indicated by $W_1$, $W_2$ and $W_3$.

A cell suspension, containing a mixture of magnetically-labeled and unlabeled cells, is pumped into the inlet port 1008, and into the flow compartment identified by its width $W_1$. The un-labeled, non-magnetic cells follow the streamlines of the flow compartment $W_1$, shown by streamline 1024, and are collected at the outlet port 1020. The low-magnetized cells cross streamlines as they travel towards the source of the magnetic energy gradient 1002, and given sufficient time, traverse the boundary streamline separating flow compartment $W_1$ from the adjacent flow compartment $W_2$. If the cell stays in the compartment $W_2$ in its travel towards the magnetic energy gradient source 1002, it is collected back in the low-magnetic cell fraction 1020 (exemplified by streamline 1026). If the cell magnetization is sufficiently high so that it traverses the entire width of the flow compartment $W_2$ and crosses to the flow compartment $W_3$, it is then collected in the high-magnetic cell fraction 1018 (exemplified by streamline 1028). Under suitable flow conditions, the most magnetic cells traverse all inlet and outlet boundary streamlines that separate flow compartment $W_1$ from the flow compartment $W_3$ and are collected at the high-magnetic cell outlet port 1018. The cells of lower magnetization stay in flow compartment $W_1$. As a result of the magnetic flow sorting of the quadrupole fractional cell sorter of the present invention, the high-magnetic cells are collected as sorted fraction 1, and the low to non-magnetic cells are collected as sorted fraction 2.

As was described in the case of the dipole fractional cell sorter of the present invention, an important feature of the quadrupole fractional cell sorter of the present invention is the ability to manipulate the sorted fractions 1 and 2 by manipulating the positions of the boundary streamlines 1016 and 1022. In particular, one may focus the stream of the cells entering the annular flow channel 1004 by selecting a small width "w1" of the respective flow channel $W_1$, by a suitable selection of a large flow rate ratio of the carrier medium 1006 to the sample feed 1012 at the inlet ports 1008 and 1014, respectively. Such focusing of the feed sample stream 1012 may be desirable in order to avoid the contamination of the magnetic cells in sorted fraction 1 by the non-magnetic cells, and thus would result in a highly specific enrichment of the medium to high-magnetic cells in sorted fraction 1 with possible losses of low-magnetic cells in sorted fraction 2. One may also de-focus the stream of the cells entering the annular flow channel 1004 by selecting a large width "w1" of the respective flow channel $W_1$ by suitable selection of a small flow rate ratio of the carrier medium 1006 to the sample feed 1012 at the inlet ports 1008 and 1014, respectively. Such de-focusing of the feed sample stream may be desirable in order to avoid the contamination of the non-magnetic cells by the magnetic cells in sorted fraction 2, and thus would result in highly specific depletion of the magnetic cells from sorted fraction 2 with possible losses of the non-magnetic cells in sorted fraction 1. One may further manipulate the sorted fractions 2 and 1 by manipulating the inlet boundary streamline 1016, outlet boundary streamlines 1022, or both, independently. The ability to control the positions of the inlet and outlet boundary streamlines leads to the precise control of the composition of the magnetic cells in sorted fractions 1 and 2, according to cell magnetization.

Moreover, one may construct a quadrupole fractional sorter with more than 2 output ports based on the inlet and outlet boundary streamlines and the flow compartments. The design would be similar to that of the dipole fractional sorter discussed above. In particular, an output port may be assigned to each flow compartment formed by the boundary streamlines.

Figure 11:
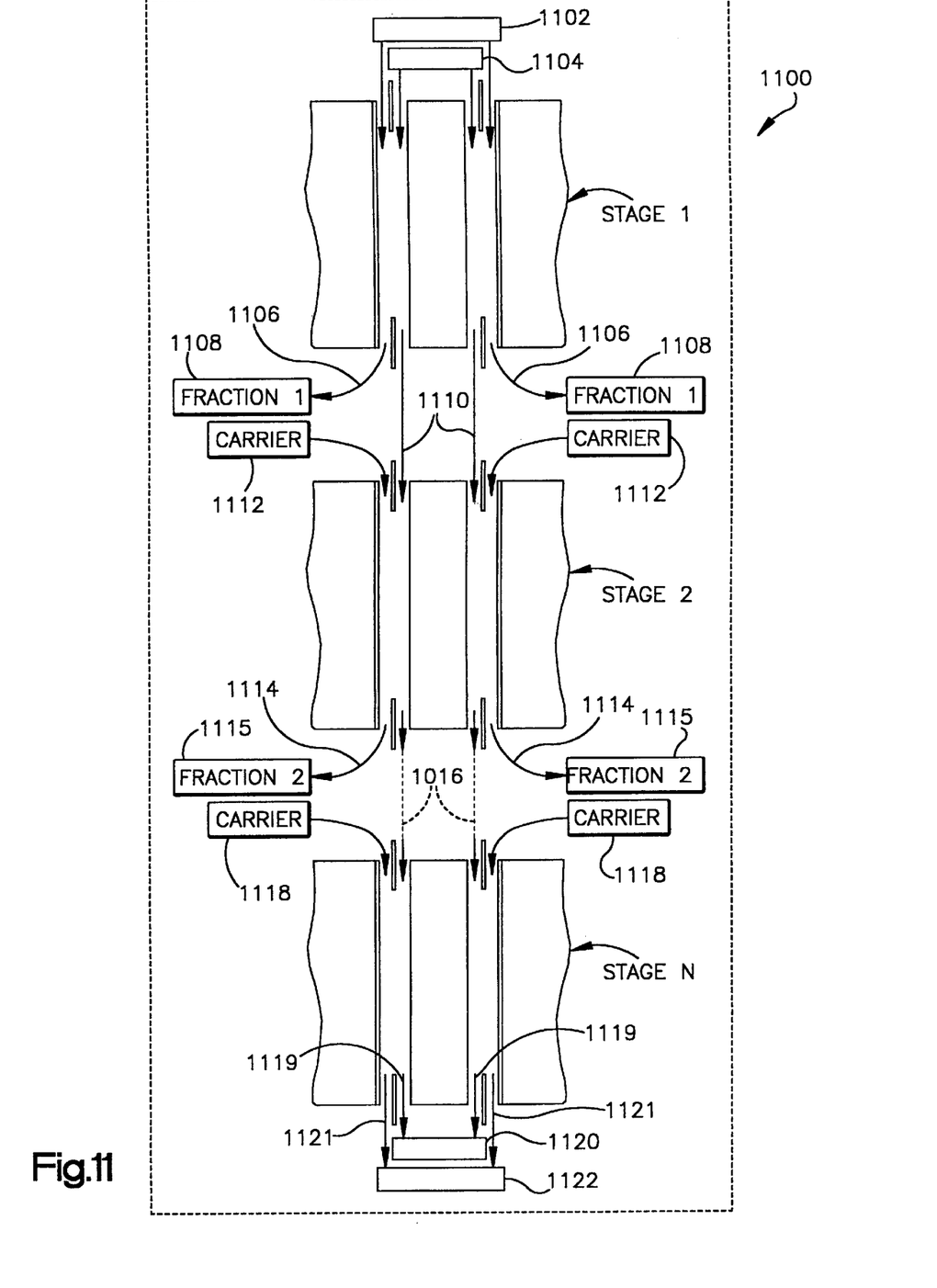
FIG. 11 is an elevated sectional view of a quadrupole fractional cell sorter having "N" stages, with each stage sorting, or removing, a range of densities.

As was described above, it is possible to sort, or remove, a range of densities of a specific cell characteristic (e.g., magnetic label) by a quadrupole fractional cell sorter which includes a plurality of stages. Illustrated in FIG. 11 is an elevated sectional view of a quadrupole fractional cell sorter 1100 having "N" stages, with each stage sorting, or removing, a range of densities $|\Delta \alpha^*|$ as defined by equation (8). More specifically, the quadrupole fractional cell sorter 1100 includes a first stage STAGE 1, a second stage STAGE 2 and an Nth stage STAGE N, a sample-in injector 1104, carrier fluid injectors 1102, 1112 and 1118 and a first and second fraction outlet port 1120 and 1122.

The operation of the multi-stage quadrupole fractional cell sorter 1100 of the present invention is similar to that of the single stage quadrupole fractional cell sorter 900 of FIG. 9. In particular, the sample-in injector 1104 injects a sample that includes the cell population, or sub-population, to be sorted into an annular space between the inlet cylindrical flow splitter and the cylindrical rod. The carrier injector 1102 injects a carrier, or suspension, medium into an annular space between the inlet cylindrical flow splitter and the annulus wall of the cylindrical flow assembly. After traversing the annular separation region, a first fraction $|\Delta \alpha^*_1|$ 1106 will exit the cylindrical flow assembly via an annular space between the annulus wall and the outlet cylindrical flow splitter and, thereafter, enter a FRACTION 1 outlet port 1108. The remaining fractions 1110 flow into the second stage STAGE 2 for further sorting. The position of the fraction $|\Delta \alpha^*_1|$ in the fractional distribution of a cell population having a density of $\alpha$ of the specific cell property of interest is shown in FIG. 5.

The second stage STAGE 2 is fundamentally similar to the first stage STAGE 1 with the exception that the sample flow (fraction flow 1110) originates from the first stage STAGE 1. As the fractional flow 1110 from the first stage STAGE 1 is injected into the second stage STAGE 2, carrier injector 1112 injects the carrier, or suspension, media. The operation of the second stage STAGE 2 is similar to that of STAGE 1 and therefore will not be further discussed. After traversing the annular separation region of the second stage STAGE 2, a second fraction $|\Delta\alpha^*_2|$ 1114 will exit the cylindrical flow assembly via the annular space between the annulus wall and the outlet cylindrical flow splitter and, thereafter, enter a FRACTION 2 outlet port 1115. The position of the fraction $|\Delta\alpha^*_2|$ is shown in FIG. 5. Note that $|\Delta\alpha^*2|$ is less than $|\Delta\alpha^*_1|$.

The remaining fractions 1116 flow into the next stage for sorting until the Nth stage STAGE N (with its associated carrier injector 1118 and sample injector, injecting the fractional flow from the N–1 stage) is traversed and the final fractional flows 1119 and 1121 arrive at fractional output ports 1120 and 1122. The position of the fraction $|\Delta\alpha^*_N|$ is also illustrated in FIG. 5. In this manner, a multi-stage quadrupole fractional cell sorter that sorts a particular fraction $|\Delta\alpha^*|$ of a cell population having a specific characteristic of interest may be implemented. The fractional distribution of the cell property of interest between fractions $|\Delta\alpha^*_i|$ where i=1 . . . N is further illustrated in FIG. 5.

In the illustrated embodiments, the quadrupole field was generated by 28 MGOe cobalt-iron-boron permanent magnets generating a magnetic flux density $B_0$ of 0.5 Tesla and a magnetic flux density gradient of 0.1 Tesla/mm at the convex surfaces 624, 630, 636 and 642 of FIG. 6. The pole pieces are constructed of soft steel, or its magnetic equivalent. The sample-in and carrier injectors, as well as the output ports, are implemented with variable flow rate syringe pumps. Additionally, in the multi-stage quadrupole fractional cell sorter of the present invention, an injector stage may be placed in flow communication between each stage so as to ensure a desired flow rate within the sorter. Furthermore, the illustrated embodiment employs, approximately, an annulus diameter of 8.8 mm, inner rod diameter of 4.8 mm, inner rod length of 196 mm, a cylindrical flow splitter length of 30 mm and width of 0.35 mm. Still further, all of the illustrated embodiments may employ a fraction determining device for determining a sorted fraction distribution inside the flow channel.

It should be further noted that, in all embodiments, the carrier medium may be varied to effect certain results. In particular, selection of the magnetic susceptibility of the carrier medium $(\chi)$ affects the $\Delta_\chi$ of the previously described equations and therefore the magnetic force $F_m$. Additionally, selection of the viscosity, density and ionic strength of the carrier medium controls the viscous drag, buoyancy and cell-to-cell interactions. Still further, one may select the electrolyte, proteins, glucose and other solute composition in order to maintain the viability and function of the cells.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. For example, the cell property $\alpha$ is not limited to the expression of surface proteins but may include other cell properties, such as the expressions of proteins, nucleic acids and other molecules inside the cell and/or cell metabolic activity, such as phagocytosis of the magnetic label. The sorting methods and apparatuses of the present invention may also be applied to other particles than cells, such as cell organelles and viruses. Moreover, the sorting methods and apparatuses of the present invention may be applied to a continuous magnetic phase in which particles or solutes are suspended or dissolved. Electromagnets and time-varying electromagnetic fields may employed instead of permanent magnets and static magnetic fields. The distribution of particles or cells between sorted fractions may, as mentioned, be controlled by adjusting the magnetic susceptibility of the carrier medium. Therefore, the invention, in its broader aspects, is not limited to the specific details, the representative apparatus, and illustrative examples shown and described. Accordingly, departures may be made from such details without departing from the spirit or scope of the applicant's general inventive concept.

We claim:

1. A cell sorting device for the fractional sorting of cells, the device comprising:
   (a) a dispensing device for providing a sample flow and a carrier flow;
   (b) a flow channel for allowing the flow of the sample and the carrier;
   (c) a first interface device for interfacing the dispensing device to the flow channel, the first interface device comprising an inlet injector region;
   (d) an aspirating device for aspirating the flow present in the flow channel;
   (e) a second interface device for interfacing the flow channel to the aspirating device, the second interface device comprising an exit port region; and
   (f) a magnetic assembly for creating a magnetic field, the magnetic assembly comprising:
      (i) a first and a second magnetic pole; and
      (ii) an air gap disposed between the first and the second magnetic poles and configured to allow at least a partial insertion of the flow channel therein.

2. The device of claim 1 wherein the exit port region of the second interface device comprises a plurality of collectors in a parallel, configuration.

3. The device of claim 1 wherein the inlet injector region of the first interface device comprises a plurality of inlet injectors in a parallel, configuration.

4. The device of claim 2 wherein the plurality of collectors are equally spaced from each other.

5. The device of claim 3 wherein the plurality of inlet injectors are equally spaced from each other.

6. The device of claim 1 wherein the flow channel comprises a symmetrical cross-sectional geometry having a substantially uniform length and a substantially uniform width, wherein the length is substantially greater than the width.

7. The device of claim 6 wherein the flow channel is positioned within the magnetic field such that the vector direction of the magnetic forces created by the magnetic field are substantially parallel to the cross-sectional length of the flow channel.

8. The device of claim 5 wherein the plurality of inlet injectors comprises a sample injector that is disposed between carrier injectors.

9. The device of claim 1 wherein
   the exit port region of the second interface device comprises a plurality of collectors,
   the inlet injector region of the first interface device comprises a plurality of inlet injectors, and
   the flow channel includes a plurality of flow compartments, and
   wherein the plurality of collectors and the plurality of inlet injectors are further configured such that each collector and each inlet injector are within a flow compartment.

10. The device of claim 1 wherein the exit port region of the second interface device comprises a plurality of collectors in a parallel, configuration,
the inlet injector region of the first interface device comprises a plurality of inlet injectors in a parallel, configuration, and
wherein the plurality of collectors and the plurality of inlet injectors are further configured such that each collector has a common center line with an inlet injector.

11. The device of claim 1 wherein the magnetic assembly is positioned substantially adjacent to the flow channel.

12. The device of claim 1 further comprising a fraction determining device for determining a sorted fraction distribution inside the flow channel.

13. The device of claim 3 wherein the plurality of inlet injectors comprises a sample injector which includes a conical-shaped discharge chamber having a large height-to-base diameter ratio.

14. The device of claim 3 wherein the plurality of inlet injectors comprises a plurality of carrier medium injectors and a sample injector and wherein the sample injector is substantially longer than the carrier medium injectors.

15. A cell sorting device for the fractional sorting of cells, the device comprising at least a first and a second stage,
   (a) wherein the first stage comprises:
      (1) a dispensing device for providing a sample flow and a carrier flow;
      (2) a first stage flow channel for allowing the flow of the sample and the carrier;
      (3) a first stage first interface device for interfacing the dispensing device to the flow channel, the first interface device comprising an inlet injector region;
      (4) a first stage second interface device for interfacing the flow channel to the second stage, the second interface device comprising an exit port region; and
      (5) a first stage magnetic assembly for creating a magnetic field, the magnetic assembly comprising:
         a. a first and a second magnetic pole; and
         b. an air gap disposed between the first and the second magnetic poles and configured to allow at least a partial insertion of the first stage flow channel therein; and
   (b) wherein the second stage comprises:
      (1) a second stage flow channel for allowing the flow of the sample and the carrier;
      (2) a second stage first interface device for interfacing the first stage to the second stage, the first interface device comprising an inlet injector region;
      (3) a second stage second interface device for interfacing the flow channel to an aspirating device for aspirating the flow present in the flow channel, the second interface device comprising an exit port region; and
      (4) a second stage magnetic assembly for creating a magnetic field, the magnetic assembly comprising:
         a. a first and a second magnetic pole; and
         b. an air gap disposed between the first and the second magnetic poles and configured to allow at least a partial insertion of the second stage flow channel therein.

16. The device of claim 15 wherein the flow channel of the first and second stages comprises a symmetrical cross-sectional geometry having a substantially uniform length and a substantially uniform width, wherein the length is substantially greater than the width.

17. The device of claim 16 wherein the flow channel of the first and second stages is positioned within the magnetic field of each stage such that the vector direction of the magnetic forces created by the magnetic field of each stage is substantially parallel to the cross-sectional length of the flow channel of each stage.

18. The device of claim 15 further comprising a fraction determining device for determining a sorted fraction distribution.

19. A cell sorting device for the fractional sorting of cells, the device comprising:
   (a) a dispensing device for providing a sample flow and a carrier flow;
   (b) an annular flow channel for allowing the flow of the sample and the carrier; the annular flow channel having an inlet and an outlet;
   (c) a first annular splitter disposed at least partially within the inlet of the annular flow channel;
   (d) a second annular splitter disposed at least partially within the outlet of the annular flow channel;
   (e) an aspirating device for aspirating the flow present in the annular flow channel; and
   (f) a magnetic assembly for creating a magnetic field, the magnetic assembly comprising:
      (i) first, second, third and forth magnetic poles; and
      (ii) an air gap disposed between the first, second, third and forth magnetic poles and configured to allow at least a partial insertion of the annular flow channel therein.

20. The device of claim 19 wherein each magnetic pole comprises a projection member having a convex surface.

21. The device of claim 20 wherein the annular flow channel further comprises an outer and inner cylindrical wall and wherein the convex surface of each magnetic pole is in physical communication with the annular flow channel outer wall.

22. The device of claim 19 wherein the first, second, third and forth magnetic poles each comprise a permanent magnet and a pole piece.

23. The device of claim 21 wherein the air gap comprises a magnetic field having a magnetic force that includes a vector direction which is radially outward towards the annular flow channel outer wall.

24. The device of claim 19 wherein the annular flow channel further comprises:
   (a) an outer wall;
   (b) an inner wall; and
   (c) an annular separation region disposed between the inner and outer walls for allowing the migration of magnetically labeled cells.

25. A cell sorting device for the fractional sorting of cells, the device comprising:
   (a) a dispensing device for providing a sample flow and a carrier flow;
   (b) an aspirating device for aspirating the flow present in the annular flow channel;
   (c) at least a first and a second sorting stage for sorting a predetermined fraction of cells having a predetermined range of densities of a particular cell characteristic, wherein the first and second sorting stages each comprise:
      (1) an annular flow channel for allowing the flow of the sample and the carrier; the annular flow channel having an inlet and an outlet;

(2) a first annular splitter disposed at least partially within the inlet of the annular flow channel;

(3) a second annular splitter disposed at least partially within the outlet of the annular flow channel; and (4) a magnetic assembly for creating a magnetic field, the magnetic assembly comprising:

(i) first, second, third and forth magnetic poles; and (ii) an air gap disposed between the first, second, third and forth magnetic poles and configured to allow at least a partial insertion of the annular flow channel therein.

26. The device of claim 25 wherein the outlet of the annular flow channel of the first sorting stage comprises a first fraction outlet port and wherein the inlet port of the annular flow channel of the second stage comprises a sample injection port and wherein the first fraction outlet port of the first sorting stage is in fluid communication with the sample injection port of the second sorting stage.

27. The device of claim 25 wherein each magnetic pole comprises a projection member having a convex surface.

28. The device of claim 25 wherein each annular flow channel further comprises:

(a) an outer wall;

(b) an inner wall; and (c) an annular separation region disposed between the inner and outer walls for allowing the migration of magnetically labeled cells.

* * * * *